US012447294B2

(12) United States Patent
Anderson et al.

(10) Patent No.: US 12,447,294 B2
(45) Date of Patent: Oct. 21, 2025

(54) FOLDABLE INHALER

(71) Applicant: 1NHALER LTD, West Linton (GB)

(72) Inventors: Gregor John McLennan Anderson, London (GB); Alan Miller Suttie, Glasgow (GB); Donald Smith, Edinburgh (GB); Lisa Charleston McMyn, West Linton (GB)

(73) Assignee: 1NHALER LTD, West Linton (GB)

(*) Notice: Subject to any disclaimer, the term of this patent is extended or adjusted under 35 U.S.C. 154(b) by 592 days.

(21) Appl. No.: 17/912,909

(22) PCT Filed: Mar. 24, 2021

(86) PCT No.: PCT/GB2021/050718

§ 371 (c)(1),
(2) Date: Sep. 20, 2022

(87) PCT Pub. No.: WO2021/191606

PCT Pub. Date: Sep. 30, 2021

(65) Prior Publication Data

US 2023/0166057 A1 Jun. 1, 2023

(30) Foreign Application Priority Data

Mar. 25, 2020 (GB) ...................................... 2004337

(51) Int. Cl.
*A61M 15/00* (2006.01)

(52) U.S. Cl.
CPC .... *A61M 15/0061* (2014.02); *A61M 15/0043* (2014.02); *A61M 2202/0064* (2013.01); *A61M 2202/064* (2013.01)

(58) Field of Classification Search
CPC .... A61M 15/00-0001; A61M 15/0028; A61M 15/0043; A61M 15/0061;
(Continued)

(56) References Cited

U.S. PATENT DOCUMENTS 5,823,182 A 10/1998 Van Oort
6,098,619 A 8/2000 Britto et al.
(Continued)

FOREIGN PATENT DOCUMENTS

CN 107243102 A 10/2017
JP 2002-542999 A 12/2002
(Continued)

OTHER PUBLICATIONS

Japanese Office Action for Application No. 2022-552374 dated Nov. 25, 2024.

(Continued)

*Primary Examiner* — Rachel T Sippel
(74) *Attorney, Agent, or Firm* — MOSER TABOADA

(57) ABSTRACT

A device for inhaling an active agent is provided that can be moved from a first configuration to a second configuration. The device comprises two flexible substrates and a membrane (40) located between the two flexible substrates, and the two flexible substrates being connected at two opposing (Continued)

edges and unconnected at two further opposing edges. An active agent provided on the membrane may be inhaled by a user when the device is in the second configuration.

17 Claims, 9 Drawing Sheets

(58) Field of Classification Search
CPC ........... A61M 15/0086–0088; A61M 15/0091; A61M 2202/064
See application file for complete search history.

(56) References Cited

U.S. PATENT DOCUMENTS

| | | | | |
|---|---|---|---|---|
| 6,245,339 | B1 | 6/2001 | Van Oort et al. | |
| 6,550,473 | B1 * | 4/2003 | Sladek .............. | A61M 15/0086 128/200.22 |
| 7,278,424 | B1 | 10/2007 | Davies et al. | |
| 10,537,693 | B2 | 1/2020 | Dennis | |
| 10,857,315 | B2 | 12/2020 | Brown | |
| 2010/0163045 | A1 | 7/2010 | Powell et al. | |

FOREIGN PATENT DOCUMENTS

| | | | |
|---|---|---|---|
| WO | WO 9956807 | A1 | 11/1999 |
| WO | WO 2019/007968 | A1 | 1/2019 |
| WO | WO 2019/008336 | A1 | 1/2019 |

OTHER PUBLICATIONS

Zhanying Zheng et al., Flow and Particle Modelling of Dry Powder Inhalers: Methodologies, Recent Development and Emerging Applications, Pharmaceutics 2021, 13, 189. https://doi.org/10.3390/pharmaceutics13020189, pp. 1 of 25.
PCT International Search Report and Written Opinion for PCT/GB2021/050718 dated Jun. 23, 2021.
UK Search Report for GB2004337.8 dated Aug. 28, 2020.
Amir Genosar et al., Affordable Needle-Free Vaccination Technology for Low Resources Settings, Aespironics Ltd., Omer Industrial Park, P.O.B 3010, Israel 84965; Aktiv-Dry LLC, 6060 Spine Road, Boulder, CO 80301 USA, 1 page.
Zhanying Zheng et al., Flow and Particle Modelling of Dry Powder Inhalers: Methodologies, Recent Development and Emerging Applications, Pharmaceutics 2021, 13, 189. https://doi.org/10.3390/pharmaceutics13020189, p. 1 of 25.

* cited by examiner

FOLDABLE INHALER

FIELD OF THE INVENTION

The invention relates to devices for delivery of active agents to a subject, more specifically to devices for delivery of active agents into the lungs of a subject, such as inhaler devices.

BACKGROUND

There are a number of active agents that are useful in treating various diseases or conditions that need to be administered to the subject via the lungs, i.e. they are pulmonary delivered active agents. Such pulmonary delivered active agents typically use devices that allow the subject to inhale the active agent directly into the lungs, such as inhalers.

Typically, inhalers in the art are designed to be used multiple times to minimise waste and to provide the subject with a single delivery system that they can carry with them to provide a reliable delivery system for when the subject needs them. For example, it is important for subjects suffering from asthma to have a delivery system to hand whenever they may suffer from an asthma attack for delivering the necessary active agent quickly and efficiently.

However, such inhaler devices have suffered from the active agent and the carrier used to allow the active agent to be successfully delivered to the lungs of the subject agglomerating and requiring the active agent and carrier to be de-agglomerated prior to use. Furthermore, many devices are intended for multiple uses and so must contain multiple doses of active agent. For each use, the active agent must be accurately and reliably metered so that each dose is the same.

Solutions to these problems involve increasingly complicated devices including de-agglomerating dispersion chambers to ensure that the active agent is suitably de-agglomerated and features to accurately meter the active agent for each dose, resulting in an increasingly bulky and less convenient device for the subject to carry and use.

Therefore, there is a need for improved inhaler devices that are convenient to carry for a subject and that are reliable.

As a result it is at least one object of the invention to provide an improved device for delivery of active agents to the lungs of a subject.

SUMMARY

According to a first aspect of the invention there is provided a device comprising two flexible substrates and a membrane located between the two flexible substrates, each of the two flexible substrates comprising at least one deformable element, the two flexible substrates being connected at two opposing edges and unconnected at two further opposing edges, wherein the device is configured to move between a first configuration where the two flexible substrates are substantially flat and in contact with one another, and a second configuration where the two flexible substrates are flexed such that a channel is formed between the two flexible substrates, wherein the membrane is configured to span the channel between the two flexible substrates when the device is in the second configuration, such that an active agent provided on the membrane may be inhaled by a user when the device is in the second configuration, wherein the at least one deformable element of each flexible substrate biases the device into a second configuration where a first opening of the channel formed between the two flexible substrates is substantially regular in shape, and a second opening of the channel formed between the two flexible substrates is substantially irregular in shape.

The inventors have surprisingly found that the device of the present aspect provides a simple way of delivering an active agent to the lungs of a subject, which is compact, mobile and easy to use.

As used herein, the term “span the channel” refers to the membrane extending across the channel to occlude at least a portion of the cross-section of the channel.

A substantially regular shape may be a shape that has an aspect ratio that is from approximately 3:1 to 1:3 or from approximately 3:2 to 2:3.

A substantially irregular shape may be a shape that has an aspect ratio that is greater than approximately 3:1 or less than approximately 1:3 or is greater than approximately 3:2 or less than approximately 2:3.

As used herein, an aspect ratio of 3:1 has a height of 3 to a width of 1 or a ratio thereof.

The first opening of the channel may be polygonal. The first opening of the channel may be substantially rectangular. For example, the first opening of the channel may be substantially oblong or square. The first opening of the channel may be substantially rectangular with curved or rounded corners.

The second opening of the channel may be comprise at least two opposed curved sides. The second opening of the channel may be biconvex. An opening that is biconvex is convex on both sides or surfaces of the opening.

Typically, the two flexible substrates are the same shape. In some embodiments the two flexible substrates may be rectangular. In some embodiments the two flexible substrates may be square. Alternatively, in other embodiments the two flexible substrates may be oblong. It will be appreciated by the person skilled in the art that alternative shapes of the two flexible substrates are included within the scope of the present disclosure, as long as the two flexible substrates are connected at two opposing edges and can move between the first configuration and the second configuration. For example, the two flexible substrates may be trapezoidal, hexagonal, octagonal or similar. In another example, the two opposed edges that are not connected may be curved.

Typically, the two flexible substrates are uniform or substantially uniform substrates that may be flexed to move from the first configuration to the second configuration. However, at least one of the two flexible substrates may comprise two or more regions that have differing rigidity such that at least one of the two or more regions is more rigid and resistant to flexing, and at least one of the two or more regions is less rigid and less resistant to flexing. For example, one or both of the flexible substrates may comprise one or more flexible portions and one or more rigid portions. The one or more rigid portions may resist flexing and the one or more flexible portions may be readily flexed. As a result during use the one or more flexible region of at least one of the two flexible substrates may flex to allow the device to move from the first configuration to the second configuration, and the one or more rigid region remains substantially planar. The flexible region may form a hinge in the flexible substrate. The flexible region may be shaped such that the device is biased towards the second configuration. In some embodiments, the or each flexible portion may correspond to an at least one deformable element, The at least one deformable element of each flexible substrate may be a scored (i.e. marked or cut) line along at least a portion of the flexible substrate. The at least one deformable element of each flexible substrate may be a flexible line extending along at least a portion of the flexible substrate. The at least one deformable element of each flexible substrate may be a crease in the flexible substrate.

The at least one deformable element of each flexible substrate may be formed by a series of perforations in the flexible substrate.

The at least one deformable element of each flexible substrate may be formed by a portion of a flexible substrate that is thinner than the majority of the flexible substrate.

Each flexible substrate may comprise a first flexible layer and a second layer that is less flexible that the firs flexible layer. The second layer may comprise a plurality of portions. each portion in the plurality of portions may be at least partially separated from one another by a space or gap. The at least one deformable element of each flexible substrate may correspond to a space or gap between adjacent portions of the second layer. Alternatively, the or each portion in the plurality of portions may abut one another forming a fault line between adjacent portions. The at least one deformable element of each flexible substrate may correspond to the fault line between adjacent portions.

The at least one deformable element may act as a hinge such that when the device moves between the first configuration and the second configuration each flexible substrate bends about the at least one deformable element.

The at least one deformable element may comprise a first portion and a second portion. The first portion may be adjacent to the first opening of the channel when the device is in the second configuration, and the second portion may be adjacent to the second opening of the channel when the device is in the second configuration. The first portion may connect to the second portion part way along the length of the flexible substrate.

The first portion may be linear or straight. The first portion may be aligned with an axis of the device that runs along the length of the channel. The first portion may be oriented at an angle to the axis of the device. For example, the first portion may be oriented at an angle of 1° to 40° to the axis of the device. The first portion may be oriented at an angle of 1° to 25° to the axis of the device. Accordingly, the first portion may extend from the first opening of the flexible substrate towards the second opening of the flexible substrate.

The first portion may be curved.

The second portion may be linear or straight. The second portion may be oriented at an angle to the axis of the device that runs along the length of the channel.

The second portion may be curved. The second portion may curve towards one of the connected edges of the flexible substrate. The second portion may curve towards one or the corners of the flexible substrate. The second portion may curve to a corner of the flexible substrate.

In embodiments where the first portion and the second portion are curved, the first portion may curve at a rate that is less than the rate of the second portion. The first portion may curve at a rate that is greater than the rate of the second portion. Accordingly, the at least two deformable elements may curved at a first rate in the portion corresponding to the first portion, and may be curved at a second rate in the portion corresponding to the second portion.

Each flexible substrate may comprise at least two deformable elements. The at least two deformable elements may be symmetrically arranged on the flexible substrate. The plane of symmetry may run along the centre line or central axis of the flexible substrate that runs along the length of the flexible substrate. The plane of symmetry may be oriented at 90° to the major plane of the flexible substrate. Accordingly, the device may be symmetrical around at least one plane of symmetry.

Moving from the first configuration to the second configuration may impose sufficient forces on the flexible substrates that they bend around the at least one deformable element.

The at least one deformable element may be configured to lock the device in the second configuration once the device is moved from the first configuration to the second configuration. Accordingly, once the device is in the second configuration, the device may be maintained in the second configuration without the application of external force by the user.

The device may further comprise at least one locking formation. The at least one locking formation may be configured to lock the device in the second configuration. The at least one locking formation may be configured to lock the device in the second configuration when the device is moved from the first configuration to the second configuration.

The at least one locking formation may be formed by at least a portion of the at least one deformable element of the first flexible substrate and the second flexible substrate. In embodiments where the at least one deformable element comprises a curved second portion, the at least one locking formation may be formed by at least a portion of the curved second portion of the at least one deformable element of the first flexible substrate and at least a portion of the curved second portion of the at least one deformable element of the second flexible substrate. The locking formation may be an indentation in the body of the device that is formed when the device is moved from the first configuration to the second configuration. The indentation may lock the device into the second configuration as the indentation is formed.

In some embodiments, the at least one locking formation may generate an audible cue when the at least one locking formation moves into a locking position. The at least one locking formation may generate a popping noise, for example.

The flexible substrates may comprise card or cardboard. The flexible substrates may comprise a polymer or plastic. The polymer or plastic may be a thermoplastic. The polymer or plastic may be a thermoplastic selected from the group consisting polypropylene (PP), polyethylene terephthalate (PET), and high-density polyethylene (HDPE). The flexible substrates may comprise a combination of card and polymer or plastic, such as a card or cardboard substrate with a polymer or plastic coating. The polymer or plastic coating may be provided on the external surface of the flexible substrates. The polymer or plastic coating may be provided on the internal surface of the flexible substrates. The polymer or plastic coating may be provided on both the internal surface and the external surface of the flexible substrates.

One or both of the two flexible substrates may be degradable. One or both of the two flexible substrates may be biodegradable. For example, the device may degrade when contacted to water, or in the presence of bacteria or similar.

The membrane and an active agent thereon may be protected from moisture, light, oxygen and contamination. The membrane may be retained within a protective pocket between the two flexible substrates. The protective pocket may open, exposing the membrane and active agent thereon when the device is moved from the first configuration to the second configuration. The protective pocket may comprise a material that is resistant to water, oxygen and/or light. For example, the protective pocket may comprise a metallic foil, such as aluminium, or a polymer or plastic film.

The membrane may be occluded by a barrier material on at least one side of the membrane when the device is in at least the first configuration. The barrier material may form a barrier membrane or a barrier film across the membrane. The barrier material and the membrane may retain the active agent between them when the device is in the first configuration. Accordingly, the active agent may be protected from the environment by the membrane and the barrier material. The barrier material may be located adjacent to the membrane. The barrier material may be located on the side of the membrane facing the first opening of the device. Accordingly, during use, air may be inhaled through the device from the second opening, through the membrane, past the barrier material to the first opening.

The barrier material may be located on each side of the membrane to form a first barrier and a second barrier such that the membrane and active agent are both retained between the first barrier and the second barrier.

The barrier material may be attached to one or more of the flexible substrates. The barrier material may be attached to the membrane. The barrier material may be attached to a substrate upon or within which the membrane is supported.

The barrier material may be breached or detached to expose the active agent when the device is moved from the first configuration to the second configuration.

The barrier material may be breached or detached to expose the active agent when a user inhales through the channel of the device when the device is in the second configuration. The barrier material may burst to expose the active agent when a user inhales through the channel of the device when the device is in the second configuration.

The barrier material may be located either side of the membrane to form a protective pocket within which the membrane and active agent are retained when the device is in the first configuration. The barrier material of the protective pocket may be broken or breached or detached when the device is moved from the first configuration to the second configuration. The barrier material of the protective pocket may be broken or breached or detached when a user inhales through the device.

The barrier material may comprise a material that is resistant to water, oxygen and/or light. For example, the barrier material may comprise a metallic foil, such as aluminium, or a polymer or plastic film.

At least a portion of at least one side of one or both of the two flexible substrates may comprise a metallic coating. For example, at least a portion of the interior surfaces of the two flexible substrates may comprise a metallic coating. The metallic coating may be a foil coating or similar. The metallic coating may comprise aluminium, copper or tin, for example.

In some embodiments, the metallic coating covers substantially the entire interior surface of both of the two flexible substrates. In some embodiments, the metallic coating covers a portion of the interior surface of both of the two flexible substrates. The portion may be adjacent to one of the unconnected opposing ends of both of the two flexible substrates. The portion may be part way between the two opposing unconnected ends of both of the two flexible substrates.

Typically, the metallic coating is located such that the membrane is at least partially covered by the metallic coating when the device is in the first configuration and the two flexible substrates are substantially flat. In some embodiments where the two flexible substrates comprise a metallic coating, the membrane is contained within an envelope or similar where the envelope comprises the metallic coating of the two flexible substrates. The envelope may be sealed such that the membrane is sealed within the envelope. Accordingly, the active agent provided on the membrane may be protected from moisture, oxygen, light and contamination.

The envelope may be sealed adjacent to the membrane. In embodiments where substantially the entire interior surface of both of the two flexible substrates is covered by the metallic coating, the envelope formed by the metallic coatings may be sealed adjacent to one or both of the unconnected opposing ends of the two flexible substrates.

The device may be a single use device. That is, the membrane between the two flexible substrates may comprise a single dose of active agent, and once the device has been used by a subject, the device may be discarded, and replaced by a new device.

In embodiments where the two flexible substrates are degradable, the discarded devices may degrade when contacted with water etc., thereby leaving minimal waste. In embodiments where the device comprises card or polymer or plastic, the device may be recycled to minimise waste.

Typically, an active agent is located on the membrane. The active agent may be on the surface of the membrane. For example, the active agent may be in particulate form and the particles may be attached to the surface of the membrane. The active agent may be loosely attached to the surface of the membrane such that when air passes through the membrane during use, the active agent is dislodged from the membrane and becomes airborne. The active agent may be bound or loosely attached to the membrane by an electrostatic charge. The electric charge applied to the membrane and/or active agent may be adjusted to ensure that the active agent is retained on the membrane prior to use, but is still lifted from the membrane during use. As a result, the active agent may be readily inhaled by a subject into their lungs.

In some embodiments, the membrane may comprise particles and the particles may comprise one or more active agents. The particles may also comprise a carrier, vehicle or excipient. The carrier, vehicle or excipient may help prevent the particles from aggregating whilst the device is in the first configuration before use. The carrier, vehicle or excipient may enhance the ability of the or each active agent to become airborne when air passes through the channel of the device when the subject inhales, for example. The carrier, vehicle or excipient may prevent the particles from aggregating on the membrane.

Typically, the active agent on the membrane is sufficient for a user to receive one full dose of the active agent when they inhale through the device. Accordingly, the amount of active agent on the membrane may correspond to a single full dose. In some embodiments, when a user inhales through the device, some active agent may remain on the membrane. Therefore, the amount of active agent on the membrane may correspond to more than a single full dose, such that the amount of active agent that is actually inhaled by the user is a full dose.

Preferably, the membrane is gas permeable to allow air to pass through the membrane during use.

The membrane may be substantially continuous and provide a substantially continuous surface upon which an active agent may be mounted. For example, the membrane may have pores that allow air to pass across the membrane but that are small enough to prevent particles of active agent to pass through.

The membrane may be a mesh. The mesh may comprise a network of fibres. The network of fibres may be woven together to form the mesh. The network of fibres may be connected at nodes to form the mesh. Particles of active agent may be adhered to the surface of the fibres of the mesh. The particles of active agent may be bound or loosely attached to the membrane by an electrostatic charge. The electric charge applied to the membrane and/or the particles of active agent may be adjusted to ensure that the particles of active agent is retained on the membrane prior to use, but is still lifted from the membrane during use.

The membrane may comprise a polymer. For example, the membrane may comprise polytetrafluoroethylene (PTFE), expanded PTFE (ePTFE), polypropylene, polyethylene, polyurethane, poly-lactic acid, poly-glycolic acid, poly-caprolactone, poly(dioxanone), or a co-polymer thereof. The membrane may comprise polyethylene or polypropylene.

In embodiments where the membrane is substantially continuous, the membrane may span only portions of the cross-section of the channel to ensure that a sufficient air flow may be created through the channel during use. Accordingly, there may be gaps in the cross-section of the channel that allow an increased air flow through the channel.

The membrane may be planar, or substantially planar. Alternatively, the membrane may comprise an indented portion. In embodiments where the membrane comprises an indented portion, a majority of the active agent on the membrane may be located within the indented portion. Accordingly, the indented portion may extend away from the outlet of the device, and towards the inlet of the device. In some embodiments, during use, the indented portion pay be everted when a user breathes in through the device. Accordingly, active agent retained within the indented portion may be propelled in the direction of airflow. The membrane may span and occlude the entire cross-section of the channel when the device is in the second configuration. Typically, the membrane spans the channel between the opposed open edges of the flexible substrates. The membrane may span or occlude a portion of the channel when the device is in the second configuration. As a result there may be portions of the channel where air can pass through the channel without passing through the membrane, and portions of the channel where air must pass through the membrane.

Typically, the membrane is flexible and is folded or collapsed when the device is in the first configuration.

The membrane may be mounted within the channel on a support. The support may comprise a gas impermeable material that occludes the channel and at least one aperture. The membrane may be mounted within the at least one aperture. Accordingly, the air flow through the channel may be constricted by the aperture within the support to thereby increase the rate of air flow through the membrane (namely, a venturi effect), thereby increasing the force exerted by the air flow on the active agent on the membrane to lift the active agent from the membrane and into the air flow.

In some embodiments, the support may comprise at least two apertures and a membrane may be supported across each aperture. Accordingly, a first membrane may be supported within a first aperture, and a second membrane may be supported within a second aperture. The first membrane may be provided with a first active agent. The second membrane may be provided with a second active agent. Therefore, the device may be configured to deliver two active agents at the same time to a user when the user inhales through the device. The first active agent may be provided in a first unit dose. The second active agent may be provided in a second unit dose. The first unit dose may be different to the second unit dose. The first unit dose may be the same as the second unit dose.

Alternatively, the first membrane may be provided with a first active agent and the second membrane may be provided with the first active agent. Accordingly, the device may provide a greater dose of the first active agent than devices with a single membrane.

The support may occlude the channel when the device is in the first configuration. The support may adopt a flexed or folded or otherwise reversibly collapsed configuration when the device is in the first configuration. When the device is moved to the second configuration, the support may open out to span and occlude the channel of the device. Typically, the support may open out to an open configuration and the support may not open any further. Accordingly, the support may ensure that the device may not be moved beyond the second configuration by a user, thereby ensuring that the optimum air flow is achieved by the device when the user inhales through the device in the second configuration.

The support may comprise at least one fold such that when the device is in the first configuration the support is folded about the at least one fold, and when the device is in the second configuration the support is extended and substantially unfolded. The at least one fold may extend across at least a portion of the membrane mounted on the support.

The support may comprise at least two folds. Each of the at least two folds may allow the support to fold in opposing directions. For example, a first fold may allow the support to be folded in a first direction, and a second fold may allow the support to be folded in an opposed second direction. When the device is in the first configuration the support may be folded about the at least two folds, and when the device is in the second configuration the support may be extended and substantially unfolded. One or more of the at least two folds may extend across at least a portion of the membrane mounted on the support.

The support may comprise at least three folds. Each of the at least three folds may allow the support to fold in opposing directions. For example, a first fold may allow the support to be folded in a first direction, a second fold may allow the support to be folded in an opposed second direction, and a third fold may allow the support to be folded in the first direction. Accordingly, the support may be folded in a concertina-type fashion. One or more of the at least three folds may extend across at least a portion of the membrane mounted on the support. The at least three folds may divide the support into at least four portions. The support may be divided into two central portions and two peripheral portions. The membrane may be mounted across an aperture in one of the four portions. The membrane may be mounted across an aperture in two of the four portions. The membrane may be mounted across the two central portions. The support may be mounted to the first flexible substrate by a first peripheral portion. The support may be mounted to the second flexible substrate by a second peripheral portion.

The support may comprise at least four folds. Each of the at least four folds may allow the support to fold in opposing directions. For example, a first fold may allow the support to be folded in a first direction, a second fold may allow the support to be folded in an opposed second direction, a third fold may allow the support to be folded in the first direction and a fourth fold may allow the support to be folded in the opposed second direction. Accordingly, the support may be folded in a concertina-type fashion. One or more of the at least four folds may extend across at least a portion of the membrane mounted on the support. Alternatively, the membrane may be located between two adjacent folds. The at least four folds may divide the support into at least five portions. The support may be divided into three central portions and two peripheral portions. The three central portions may comprise a middle portion in between two adjacent portions. The membrane may be mounted across an aperture in one of the four portions. The membrane may be mounted across two of the four portions. The membrane may be mounted across an aperture in the middle portion. The support may be mounted to the first flexible substrate by a first peripheral portion. The support may be mounted to the second flexible substrate by a second peripheral portion.

The support may comprise or form an enclosure when folded. The active agent may be located on the side of the membrane that is on the inside of enclosure of the folded support when the device is in the first configuration. Accordingly, the active agent may be protected within the enclosure prior to use. In embodiments where the support comprises at least four folds, the membrane may be located within the enclosure when the support is folded.

The support may comprise a seal adjacent to the edge of the enclosure when the support is folded. The seal may protect the active agent when the device is in the first configuration.

The support may be located in the middle of the channel such that the support is substantially equidistant from the first opening and the second opening. The support may be located adjacent to or closest to the first opening. The support may be located adjacent to or closest to the second opening.

Typically, the membrane is configured to ensure that during use when a subject inhales at one of the openings of the channel the air flow through the device is sufficient to dislodge a sufficient amount of the active agent or particles comprising the active agent from the membrane into the lungs of the subject to provide the dose of active agent required.

Preferably, the active agent is effective when delivered to the lungs of the subject. Therefore, the device of the present aspect is suitable for use for delivery of any active agent that may be delivered to the lungs of a subject.

Typically, the active agent is provided as a dry powder. The dry powder may comprise particles. The particles may comprise the active agent. The particles may comprise a carrier.

The active agent may be a bronchodilator. For example, the active agent may be salbutamol, salmeterol, formoterol, Ventolin, or other such active agent.

The active agent may be a vaccine. For example, the active agent may be an inhalable vaccine against diseases such as cholera, diphtheria, anthrax, tetanus, hepatitis A or B, influenza, measles, meningitis, polio, rabies, pneumonia, rotavirus, smallpox, typhoid, yellow fever etc.

The active agent may treat pain. For example, the active agent may be an inhalable form of tramadol, gabapentin, Vicodin (registered trade mark), ibuprofen, acetaminophen, hydrocodone, naproxen, methadone, codeine, hydroxyzine, paracetamol, aspirin, etc.

The active agent may be used to treat diabetes. For example, the active agent may be an inhalable form of insulin, canagliflozin, alogliptin benzoate, dapagliflozin, empagliflozin, ranibizumab, duglaglutide, pioglitazone hydrochloride and glimepiride etc.

The active agent may be used to treat or prevent migraine. The active agent may be a triptan (or 5HT agonists) such as Almotriptan (such as Almogran™), Eletriptan (such as Relpax™), Frovatriptan (such as Migard™), Naratritan (such as Naramig™), Rizatriptan (such as Maxalt™), Sumatriptan (such as Imigran™), Zolmitriptan (such as Zomig™) metoclopramide, rimegepant, lasmiditan, or similar.

The active agent may be a hormone, such as an inhalable form of oxytocin or similar. The active agent may prevent postpartum haemorrhage.

The active agent may be used to treat sexual health disorders. For example, the active agent may be an inhalable form of sildenafil, tadalafil or vardenafil.

The active agent may be used to treat nausea. For example, the active agent may be an inhalable form of ondansetron, domperidone, dolasetron, or dronabinol.

The active agent may be used to treat allergies. For example, the active agent may be an inhalable form of loratadine, cetirizine, chlorphenamine, diphenhydramine, or fexofenadine.

The active agent may be used to treat epilepsy. For example, the active agent may be an inhalable form of levetiracetam, lacosamide, or lamotrigine.

The active agent may be used to treat asthma.

The active agent may be used to treat multiple sclerosis and/or related symptoms. For example, the active agent may be an inhalable form of teriflunomide, or fingolimod.

The active agent may be used to treat Parkinson's disease. For example, the active agent may be an inhalable form of pramipexole, rotigotine, ropinirole, carbidopa-levodopa.

The active agent may be used to treat motor neurone disease (MND) and/or related symptoms. For example, the active agent may be an inhalable form of riluzole.

The active agent may also be a vitamin, a dietary supplement, a probiotic, or a natural stimulant such as caffeine, or a natural relaxant such as chamomile extract, or a herbal remedy. The active agent may be any other non-medical, inhalable agent that can be manufactured as an inhalable dry powder.

The first opening of the channel may be an air outlet and the second opening of the channel may be an air inlet such that during use air is taken into the channel via the air inlet and inhaled out of the channel via the air outlet. Accordingly, the air inlet may have an irregular shape and the air outlet may have a regular shape such that the flow of air through the channel is accelerated from the air inlet towards the air outlet. The active agent may be provided on one side of the membrane. The active agent may be provided on the side of the membrane facing the air outlet.

The device may be protected from moisture. The device may be stored in waterproof packaging before use. The device may comprise one or more seals. The device may comprise one or more seals such that the membrane is sealed within the device and is thereby protected from moisture. For example, the device may comprise a seal adjacent to each opening. In another example, the device may comprise a seal either side of the membrane. During use, the action of moving the device from the first position to the second position may break the or each seal such that the membrane and any active agent mounted thereon is exposed.

In embodiments where the two flexible substrates comprise a metallic coating, the device may comprise seals at each opening of the channel and seals at either side of the metallic coating.

The device may comprise one or more reinforcing elements. The or each reinforcing element may bias the device toward the second configuration. The or each reinforcing element may provide a biasing force that is insufficient to move the device from the first configuration to the second configuration, and complements the force applied by a user to open or move the device from the first configuration to the second configuration.

The device may comprise one or more reinforcing elements in a central region of the device. The device may comprise one or more reinforcing elements adjacent to one or more of the openings of the channel. The reinforcing elements may allow the device to more readily move from the first configuration to the second configuration when a threshold pressure is applied by the user to the two opposing connected edges.

The or each reinforcing element may extend across one or both flexible substrates. The or each reinforcing element may extend across the width of the channel. That is, the or each reinforcing element may extend between the connected edges of the or each flexible substrate.

The or each reinforcing element may be shaped to promote opening of the channel when the two flexible substrates are flexed. For example, the or each reinforcing element may be curved or bent such that when pressure is applied to the connected opposing edges, the device is biased toward the second configuration.

The device may be dimensioned to fit within a user's hand. In some embodiments the device may be dimensioned to fit within a user's wallet or purse. For example, the device may be the size of a typical credit card or similar (i.e. generally planar having two major dimensions approximately 80-90 mm by 50-60 mm, such as 86 mm by 54 mm, for example). As a result, the device may be retained by a user in their wallet or purse to ensure that the device is readily to hand should the user require a dose of the active agent.

In some embodiments, the channel is configured to optimise air flow through the channel.

The cross-section of the channel may decrease from the air inlet to the air outlet, such that the air flow through the channel is accelerated from the air inlet to the air outlet.

The cross-section of the channel may be reduced in a portion of the channel. The cross-section of the channel may be reduced in a portion of the channel between the air inlet and the air outlet.

Typically, the height of the channel in one dimension may be greater at the second opening than at the first opening. The width of the channel may be greater at the first opening than at the second opening. For example, the height of the channel when viewed from the side may be greater at the second opening that at the first opening, and the width of the channel when viewed from above may be greater at the first opening than at the second opening.

In at least one embodiment, the cross-section of the channel may have a "trumpet-like" shape The channel may comprise a first portion and a second portion. In at least one dimension, the cross-section of the channel within the first portion may be larger than the cross-section of the second portion. In at least one dimension, the cross-section of the channel within the first portion may be smaller than the cross-section of the second portion. Accordingly, where the rate of air flow is constant through the channel, the air must travel more quickly through the second portion compared to the first portion.

The second portion may comprise an aperture that constricts the channel. The membrane may span the aperture such that air flowing through the second portion must flow through the membrane. Accordingly, the air is moving faster through the membrane than through the first portion of the channel, thereby imposing a greater force on the active agent present on the membrane to lift that active agent into the air flow.

In some embodiments the channel may extend across the full width of the two flexible substrates. In alternative embodiments, the channel may extend across only a portion of the full width of the two flexible substrates. The two flexible substrates may comprise features such as creases or more pliant portions that define the width of the channel. For example, the two flexible substrates may comprise creases that run along the length of the two flexible substrates and that are spaced from the opposed connected edges of the two flexible substrates. During use, when the user moves the device from the first configuration to the second configuration, the channel is formed between the two creases, and the two flexible substrates remain substantially flat between the crease and associated connected edge either side of the channel.

The device may comprise an element that restricts the maximum extent to which the two flexible substrates can be flexed to move the device to the second configuration. For example, the device may comprise one or more connectors attached to each of the two flexible substrates such that when the device is in the second configuration, the separation of the two flexible substrates is determined by the length of the or each connector. The one or more connectors may be attached to the interior surface of each of the two flexible substrates within the channel. The one or more connectors may be attached to the exterior surface of each of the two flexible substrates. Alternatively, the device may comprise one or more connectors that extend across the width of the device that restrict the maximum extent to which at least one of the two flexible substrates may be bent. The device may comprise a rigid tertiary structure or a triangular lock fold that define the maximum extent the channel of the device may open.

The device may comprise a mouthpiece adjacent to or at the air outlet. Accordingly, during use the user may contact their mouth to the mouthpiece when the device is in the second configuration and then inhale through the mouthpiece. The mouthpiece may be the air outlet. The mouthpiece may be configured to provide support to the lips of a user during use.

The invention extends in a second aspect to a method of using a device according to the first aspect, the method comprising the steps:

(i) providing a device according to the first aspect;
(ii) applying pressure to the two opposed connected edges of the two flexible substrates of the device to thereby move the device from the first configuration, to the second configuration; and
(iii) inhaling adjacent to an opening of the device in the second configuration to thereby inhale an active agent from the membrane of the device through the channel and into the lungs.

When the device is in the second configuration, the user may contact their mouth to an opening of the channel. Therefore, the user may inhale through the device in step (iii). A seal may be formed between the device and the mouth of the user. Accordingly, when the user inhales, all or substantially all air that passes into the user's mouth has passed through the channel of the device and thereby carries active agent from the membrane of the device.

The user may apply pressure to the two opposed edges of the two flexible substrates by squeezing those edges toward each other.

In embodiments where the device comprises seals, step (ii) typically breaks said seals to thereby expose the membrane of the device.

In embodiments where the device is provided in packaging, the device is typically removed from said packaging prior to step (ii).

Once the user has inhaled through the device, the device may be discarded.

In some embodiments, the device may lock when moved from the first configuration to the second configuration to thereby lock the device in the second configuration. Accordingly, the device may be retained in the second configuration without continued application of force by the user.

According to a third aspect of the invention there is provided a device comprising two flexible substrates and a membrane located between the two flexible substrates, each of the two flexible substrates comprising at least one deformable element, the two flexible substrates being connected at two opposing edges and unconnected at two further opposing edges, wherein the device is configured to move between a first configuration where the two flexible substrates are substantially flat and in contact with one another, and a second configuration where the two flexible substrates are flexed such that a channel is formed between the two flexible substrates, wherein the membrane is configured to span the channel between the two flexible substrates when the device is in the second configuration, such that an active agent provided on the membrane may be inhaled by a user when the device is in the second configuration, wherein the at least one deformable element of each flexible substrate biases the device into a second configuration where a first opening of the channel formed between the two flexible substrates is substantially rectangular, and a second opening of the channel formed between the two flexible substrates is substantially biconvex.

Optional and preferred features of the device of the first aspect are optional and preferred features of the device of the third aspect where appropriate and where there is no contradiction with features described in the third aspect.

BRIEF DESCRIPTION OF THE FIGURES

Embodiments of the present invention will now be described, by way of non-limiting example, with reference to the accompanying drawings.

DETAILED DESCRIPTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as “a”, “an” and “the” are not intended to refer to only a singular entity, but include the general class of which a specific example may be used for illustration. The terminology herein is used to describe specific embodiments of the invention, but their usage does not delimit the invention, except as outlined in the claims.

Figure 1:
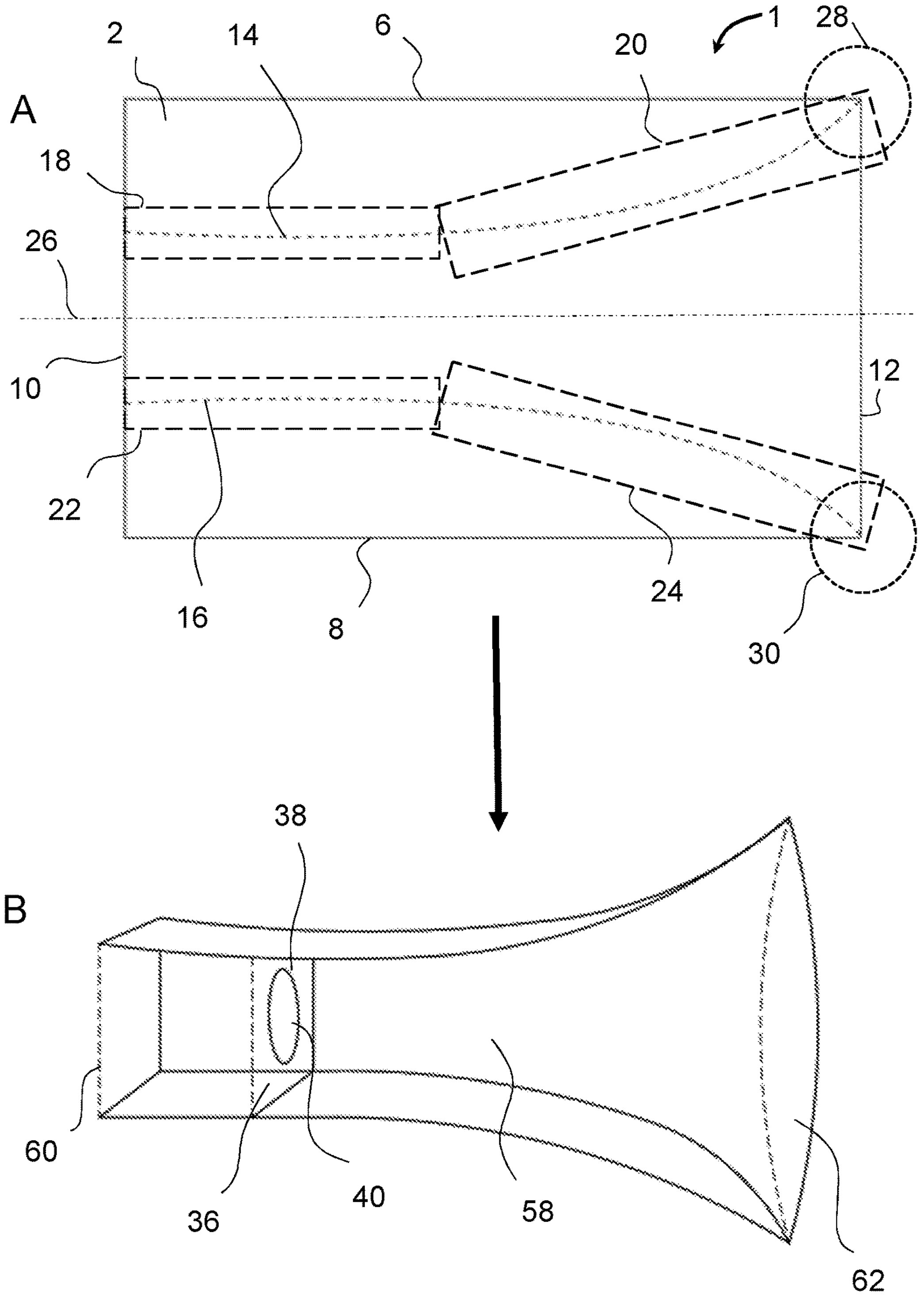
FIG. 1: a device according to an embodiment showing the device A) in the first configuration and B) in the second configuration.
Figure 2A:
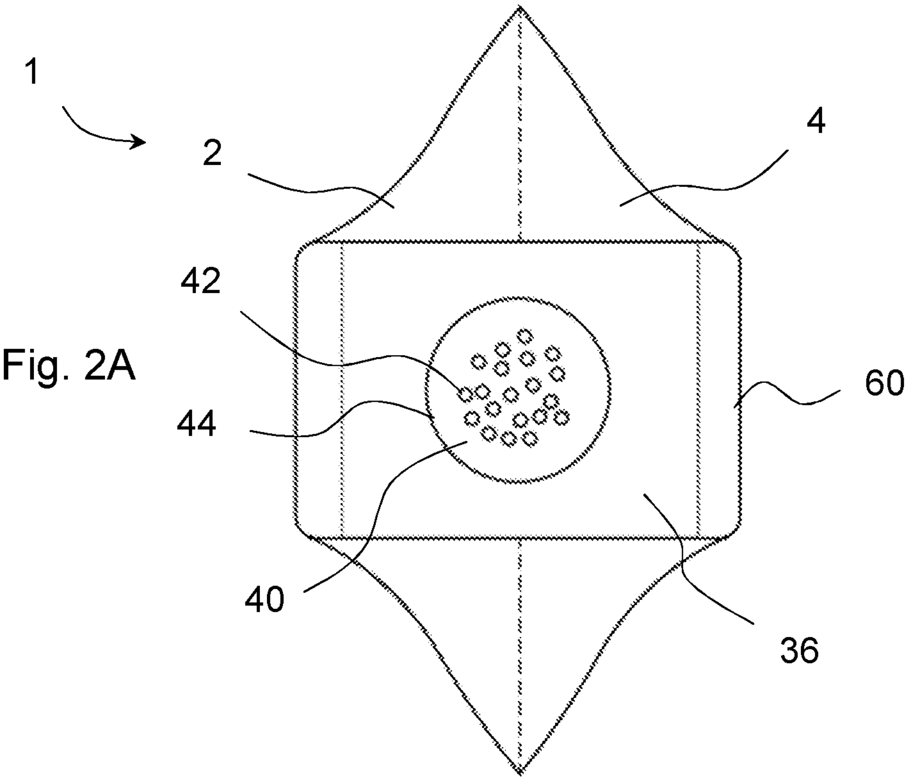
FIG. 2: a device according to an embodiment in the second configuration A) viewed from the front (outlet end) and B) viewed from behind (inlet end)
Figure 2B:
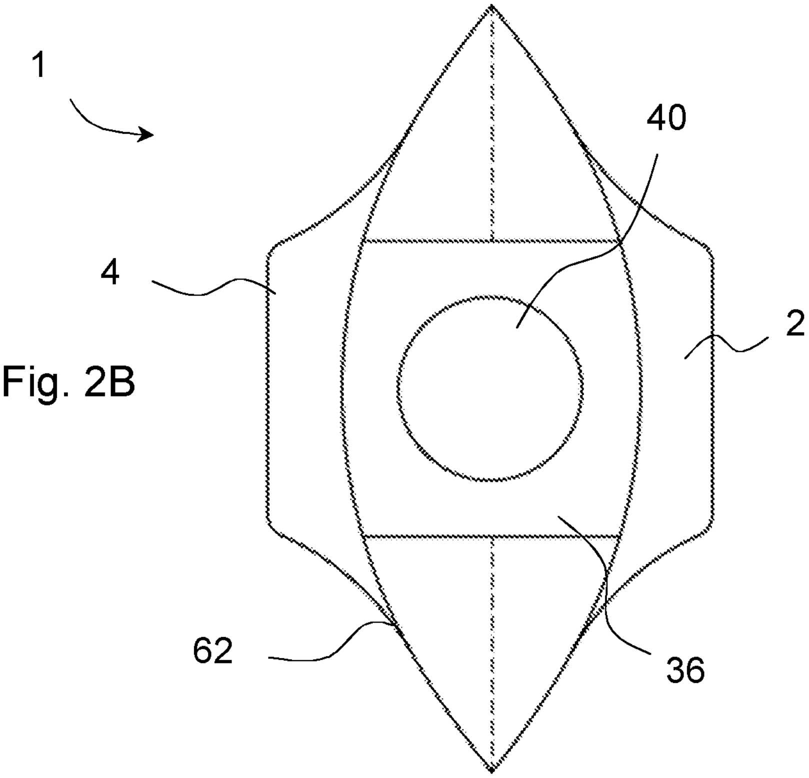

With reference to FIGS. 1 and 2, there is provided a device 1 comprising a first flexible substrate 2 and a second flexible substrate 4. The first flexible substrate 2 and the second flexible substrate 4 are rectangular. The first flexible substrate 2 and the second flexible substrate 4 are connected to one another along a first edge 6 and along a second edge 8 opposed to the first edge 6. The first flexible substrate 2 and the second flexible substrate 4 are not connected to one another along a third edge 10 and along a fourth edge 12 opposed to the third edge 8.

The first flexible substrate 2 comprises a first scored line 14 (acting as a first deformable element) and a second scored line 16 (acting as a second deformable element). The first scored line 14 comprises a linear portion 18 (acting as a first portion of the first deformable element) and a curved portion 20 (acting as a second portion of the first deformable element). The second scored line 16 comprises a linear portion 22 (acting as a first portion of the second deformable element) and a curved portion 24 (acting as a second portion of the second deformable element). The first scored line 14 and the second scored line 16 are arranged symmetrically about a central axis 26 running along the length of the first flexible substrate 2. The curved portion 24 of the first scored line 14 extends from the linear portion 22 to a first corner 28 of the first flexible substrate 2. The curved portion 24 of the second scored line 16 extends from the linear portion 22 of the second scored line 16 to a second corner 30 of the first flexible substrate 2.

The second flexible substrate 4 comprises a first scored line 32 and a second scored line 34 that correspond to the first scored line 14 and second scored line 16 of the first flexible substrate 2.

Figure 3A:
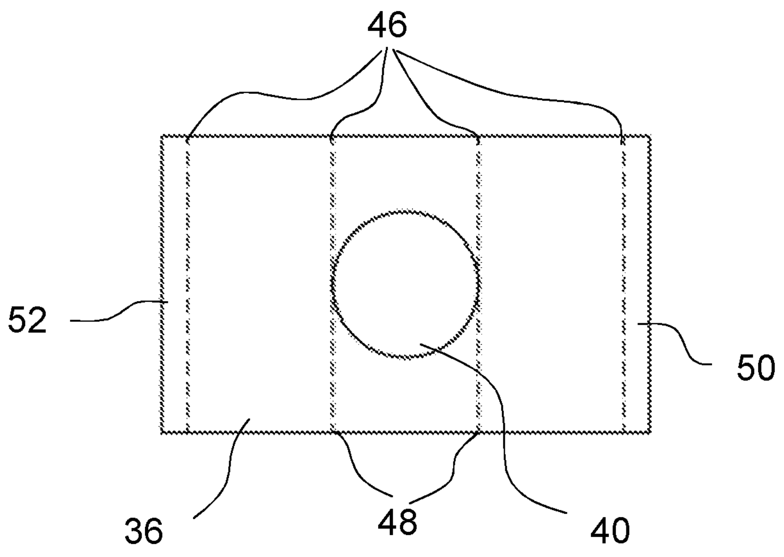
FIG. 3: a membrane support according to an embodiment A) in a flat configuration and B) in a folded configuration.
Figure 3B:
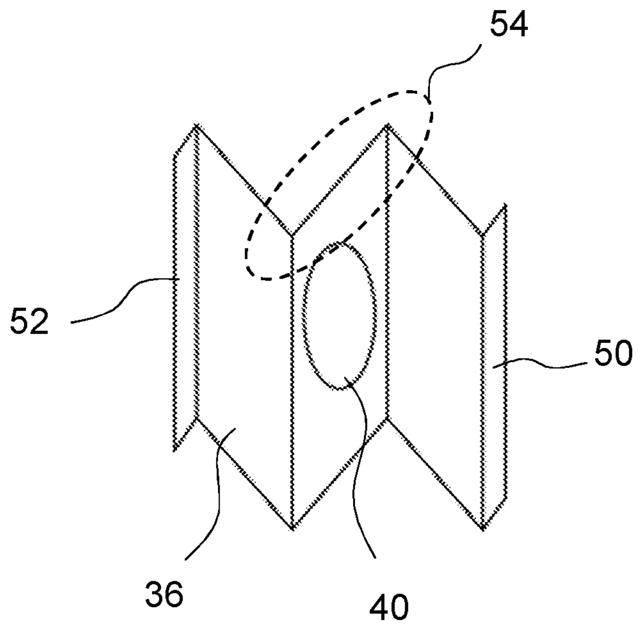

With reference to FIGS. 3A and 3B, the device 1 further comprises a support 36 located between the first flexible substrate 2 and the second flexible substrate 4. The support 36 comprises an aperture 38 that is spanned by a membrane 40. An inhalable form of an active agent 42 is supported on a first side 44 of the membrane 40. As shown in FIGS. 3A and 3B, the support 36 has four folds 46 such that the support 36 can be folded in a concertina-like fashion (see FIG. 3B, for example). The membrane 40 is located centrally on the support 36 with a fold 48 either side of the membrane 40. The support 36 is further folded adjacent to the sides to provide a first attachment surface 50 and a second attachment surface 52 that is used to contact and be fixed to the first flexible substrate 2 and the second flexible substrate 4 respectively. Accordingly, when the support 36 is folded about the four folds 46 the membrane 40 is retained within a pocket 54 (corresponding to an enclosure) such that the active agent 42 supported on the membrane 40 is protected.

Prior to use the device 1 is in a first configuration 56 where the first flexible substrate 2 and the second flexible substrate 4 are substantially flat and the support 36 is folded between the first flexible substrate 2 and the second flexible substrate 4.

During use, a user applies force to the first and second edges 6, 8 where the first flexible substrate 2 is connected to the second flexible substrate 4. This application of force flexes the first flexible substrate 2 and the second flexible substrate 4 outward from one another. As the first flexible substrate 2 and the second flexible substrate 4 flex they bend about the first scored line 14 and the second scored line 16 until the device 1 is in the second configuration. Accordingly, a channel 58 is formed between the first flexible substrate 2 and the second flexible substrate 4 having a rectangularly-shaped first end 60 and a biconvex-shaped second end 62 such that the height of the second end 62 is significantly greater that the height of the first end 60, and the width of the second end 62 is significantly less than the width of the first end 60.

In addition, the support 36 unfolds such that the support 36 spans the channel 58 and is located closer to the first end 60 of the channel 58 than to the second end 62 of the channel 58.

The user then inserts the first end 60 of the device 1 into their mouth and inhales through the device 1. At least a portion of the active agent 42 supported on the membrane 40 spanning the channel 58 is lifted from the membrane 40 and is inhaled by the user.

Figure 4A:
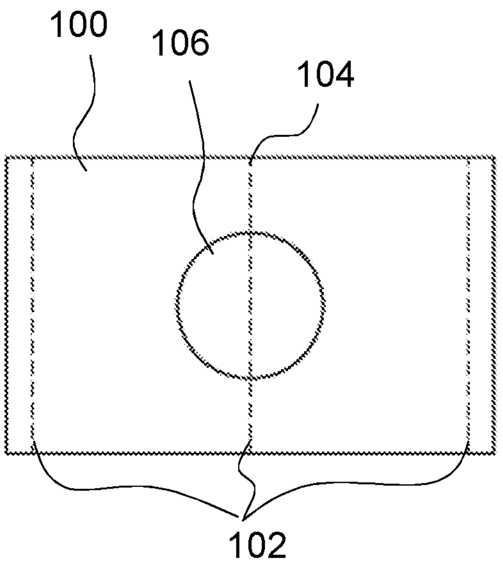
FIG. 4: a membrane support according to an embodiment A) in a flat configuration and B) in a folded configuration.
Figure 4B:
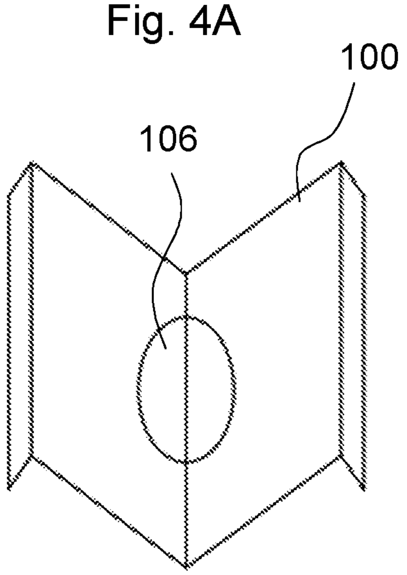
Figure 5:
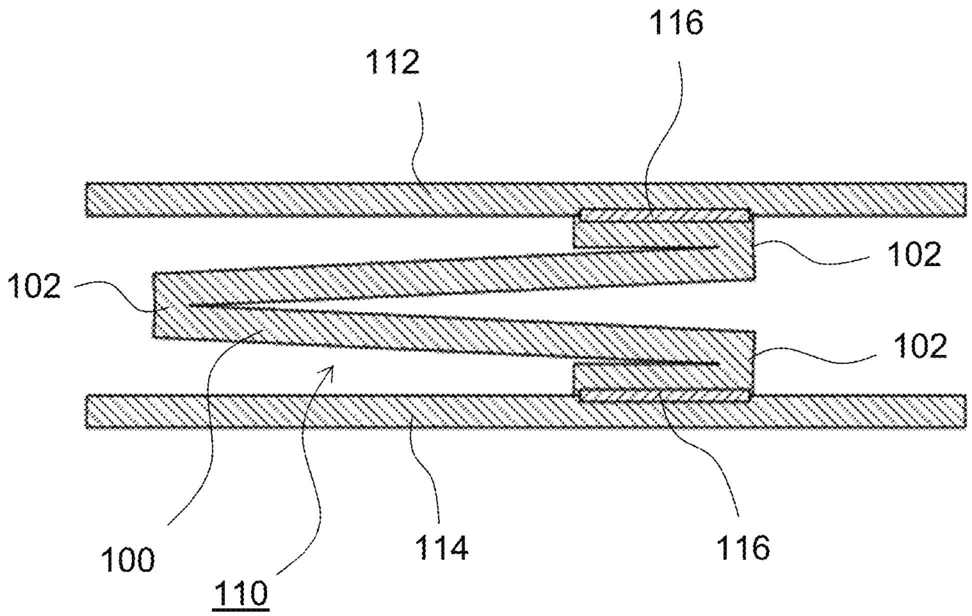
FIG. 5: a side view of a membrane support according to an embodiment in a folded configuration.

Once the active agent 42 has been inhaled the device 1 may be disposed of by the user. With reference to FIGS. 4A, 4B and 5, in an alternative embodiment the support 100 comprises three folds 102 with a fold running through the middle 104 of the membrane 106 as shown in FIGS. 4A and 4B. FIG. 5 shows a side view of the support 100 in a folded configuration 110 attached to the first flexible substrate 112 and the second flexible substrate 114 by welds 116.

Figure 6A:
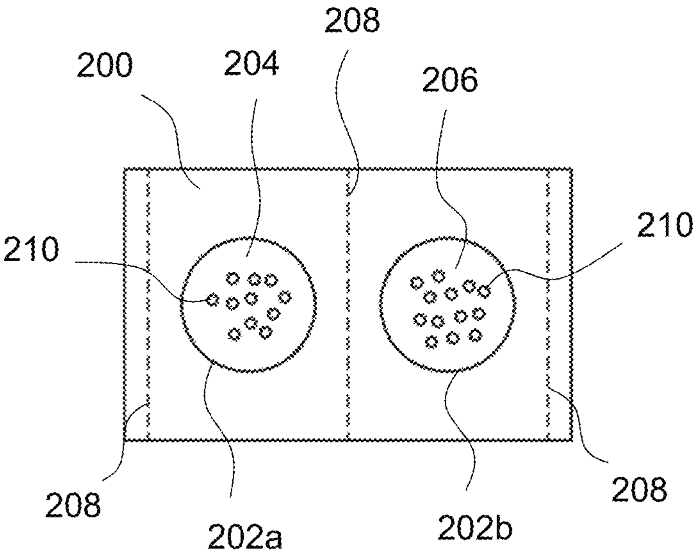
FIG. 6: a membrane support according to an embodiment A) in a flat configuration and B) in a folded configuration.
Figure 6B:
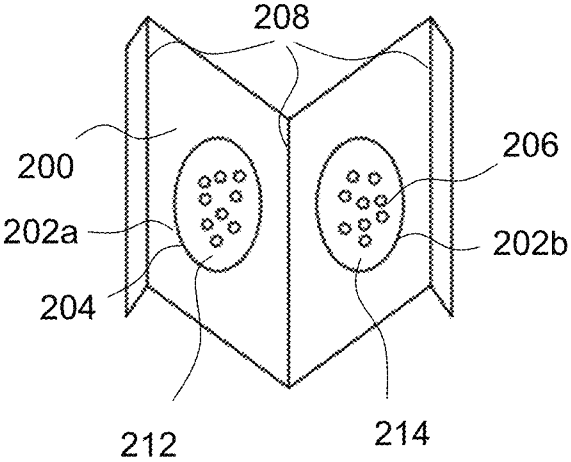

In a further alternative embodiment with reference to FIGS. 6A and 6B the support 200 comprises a first aperture 202*a* and a second aperture 202*b* with a first membrane 204 spanning the first aperture 202*a* and a second membrane 206 spanning the second aperture 202*b*. The support 200 comprises three folds 208 with a fold located between the first 202*a* and second 202*b* apertures and first 204 and second 206 membranes. The first membrane 204 supports a first active agent 210 and the second membrane 206 also supports the first active agent 210. Accordingly, the device is configured to deliver a higher dose of the first active agent 210 than devices having supports comprising a single membrane.

Alternatively, the first membrane 204 supports a first active agent 212 and the second membrane 206 supports a second active agent 214. Accordingly, the device is configured to deliver two active agents at the same time.

Figure 7A:
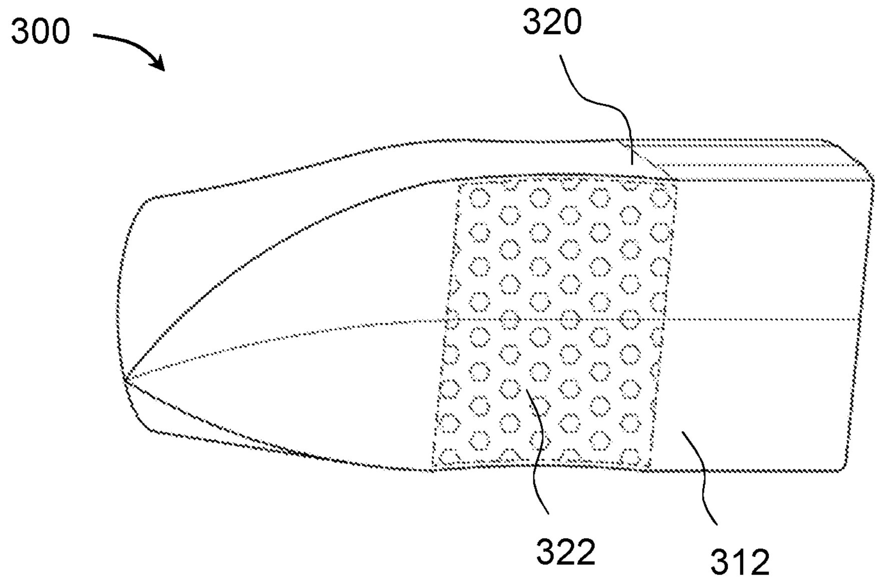
FIG. 7: a view of a device according to an embodiment from A) a top view, B) a side view, and C) a perspective view.
Figure 7B:
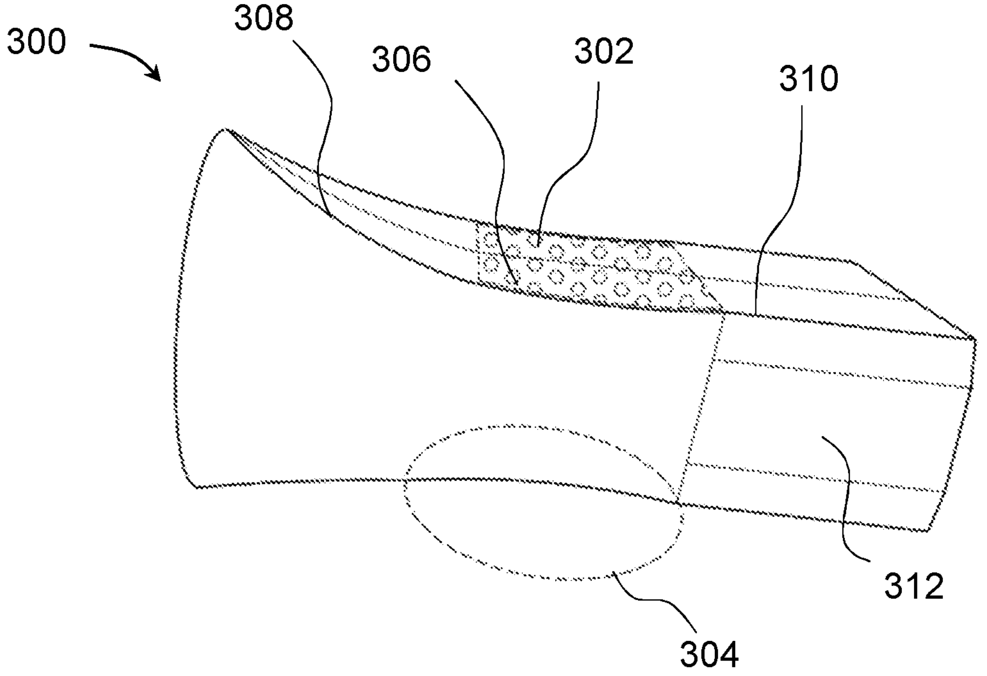
Figure 7C:
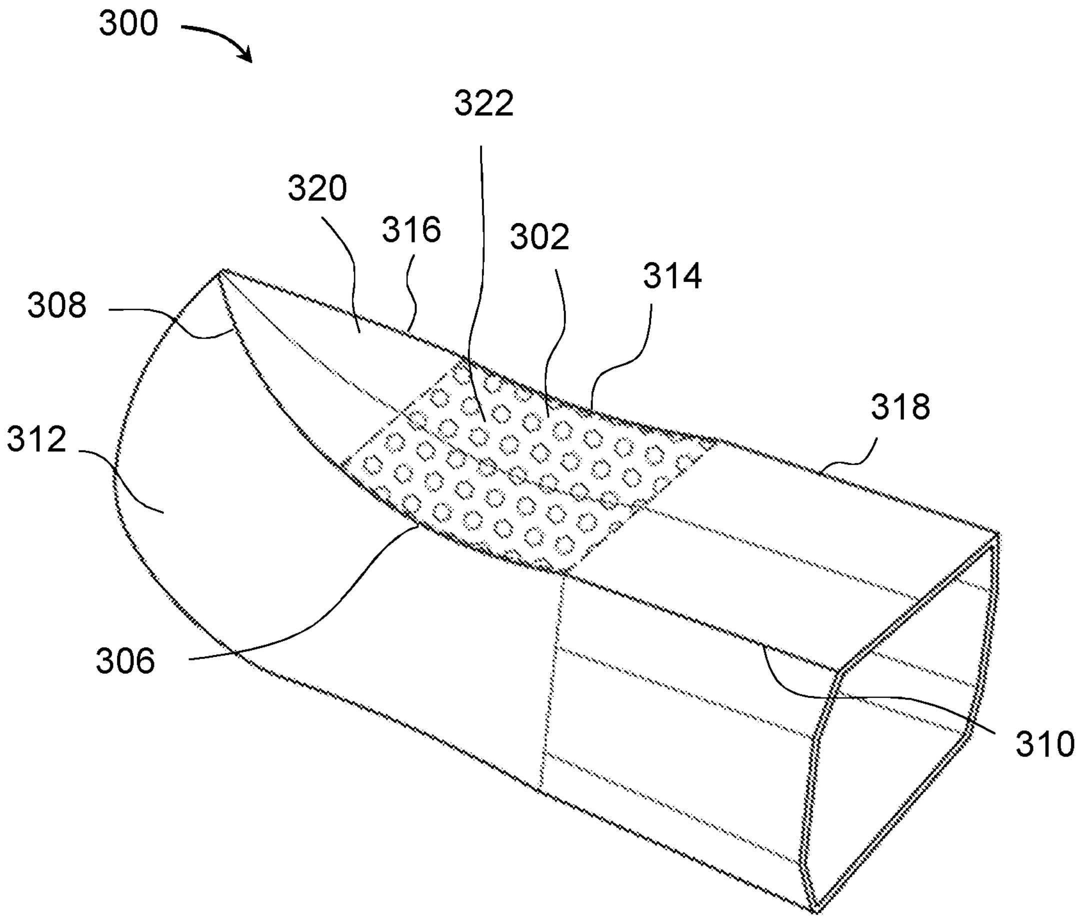

In a still further embodiment with reference to FIGS. 7A, 7B, and 7C, the device 300 comprises a first locking formation 302 and a second locking formation 304. The first locking formation 302 is formed by a first part 306 of the curved portion 308 of the first scored line 310 of the first flexible substrate 312 and a first part 314 of the curved portion 316 of the first scored line 318 of the second flexible substrate 320. As the device 300 is moved from the first configuration to the second configuration the first locking formation 302 and the second locking formation 304 are pushed by the user until they pop into a locking position. Accordingly, the device is locked into the second configuration such that the user is not required to maintain a force to retain the device 300 in the second configuration.

The first flexible substrate 312 and the second flexible substrate 320 comprises a gripping portion 322. The gripping portion 322 has a textured surface to enhance the ability of the user to grip the device in the second configuration and may act as an indication to the user where force should be applied to move the device from the first configuration to the second configuration.

Figure 8A:
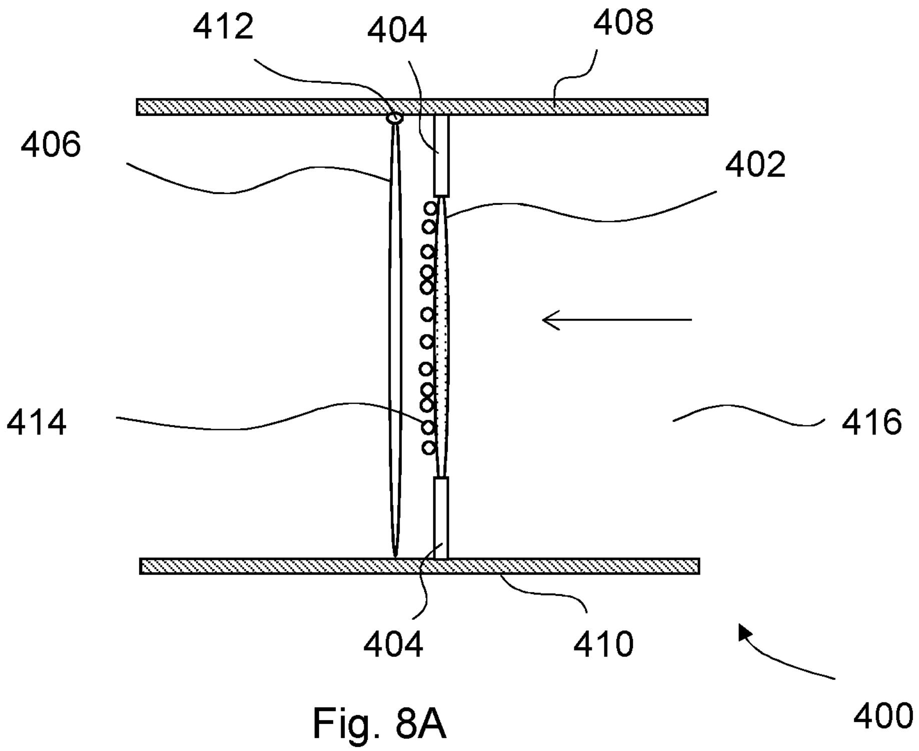
FIG. 8: a schematic side view of a section of a device according to an embodiment A) before and B) during inhalation.
Figure 8B:
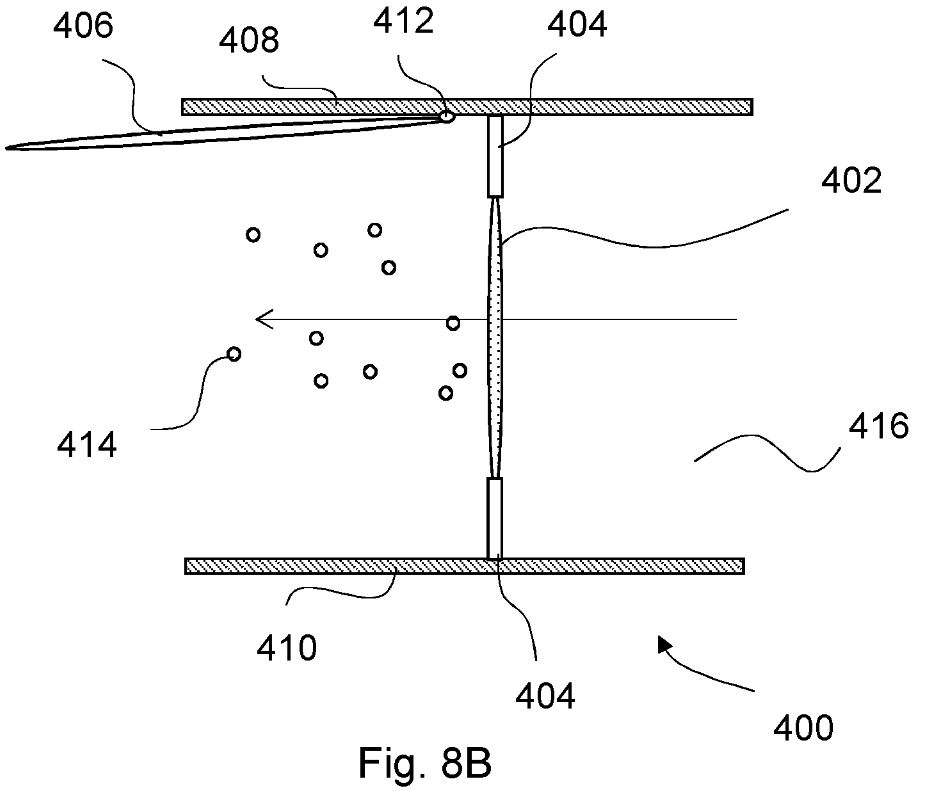

In an alternative embodiment with reference to FIGS. 8A and 8B, a device 400 according to any of the previously described devices further comprises a membrane 402 mounted within a support 404 and a barrier film 406 (acting as a barrier material) located between a first flexible substrate 408 and a second flexible substrate 410. The barrier film 406 is welded to the first flexible substrate 408 at weld 412 and is releasable attached to the second flexible substrate 410 in the first configuration. An active agent 414 is retained between the barrier film 406 and the membrane 402 prior to use. When the device 400 is moved to the second configuration the membrane 402 occludes the channel 416 formed between the first flexible substrate 408 and the second flexible substrate 410 and the barrier film 406 detaches from the second flexible substrate 410. During use the user inhales through the channel 416 and the barrier film 406 pivots about the weld 412 away from second flexible substrate 410 towards the first flexible substrate 408 to thereby release the active agent 414 from the membrane 402 to the user.

It will be appreciated by the person skilled in the art that the above embodiments are examples and that the features of each disclosed embodiment may be combined with the features of other embodiments. Further variations and modifications are herein contemplated and included in the present invention.

The invention claimed is:

1. A device comprising two flexible substrates and a membrane located between the two flexible substrates, each of the two flexible substrates comprising at least one deformable element, the two flexible substrates being connected at two opposing edges and unconnected at two further opposing edges, wherein the device is configured to move between a first configuration where the two flexible substrates are substantially flat and in contact with one another, and a second configuration where the two flexible substrates are flexed such that a channel is formed between the two flexible substrates, wherein the membrane is configured to be positioned within the channel between the two flexible substrates when the device is in the second configuration, such that an active agent provided on the membrane may be inhaled by a user when the device is in the second configuration, wherein the at least one deformable element of each flexible substrate biases the device into a second configuration where a first opening of the channel formed between the two flexible substrates is substantially regular in shape, and a second opening of the channel formed between the two flexible substrates is substantially irregular in shape.

2. The device according to claim 1, wherein the two flexible substrates are rectangular.

3. The device according to claim 1, wherein the at least one deformable element of each flexible substrate is a scored line along at least a portion of the flexible substrate, a flexible line extending along at least a portion of the flexible substrate, or a crease in the flexible substrate.

4. The device according to claim 1, wherein the at least one deformable element comprises a first portion and a second portion.

5. The device according to claim 4, wherein the first portion is linear or straight.

6. The device according to claim 4, wherein the second portion is curved.

7. The device according to claim 1, wherein the at least one deformable element of a first flexible substrate of the two flexible substrates comprises at least two deformable elements and the at least one deformable element of a second flexible substrate of the two flexible substrates comprises at least two deformable elements.

8. The device according to claim 7, wherein the device further comprises at least one locking formation.

9. The device according to claim 1, wherein the membrane is mounted within the channel on a support.

10. The device according to claim 9, wherein the support comprises an aperture and the membrane spans the aperture to thereby occlude the channel.

11. The device according to claim 9, wherein the support comprises at least one fold such that when the device is in the first configuration the support is collapsed into a folded state and when the device is in the second configuration the support is expanded into an open state.

12. The device according to claim 11, wherein the support forms an enclosure when in the folded state and the active agent is protected within the enclosure.

13. The device according to claim 1, wherein the height of the channel is greater at the second opening than at the first opening and the width of the channel is greater at the first opening than at the second opening.

14. The device according to claim 1, wherein the device is trumpet shaped.

15. A method of using the device according to claim 1, the method comprising the steps:

(i) providing the device according to claim 1;

(ii) applying pressure to the two opposed connected edges of the two flexible substrates of the device to thereby move the device from the first configuration, to the second configuration; and (iii) inhaling adjacent to the first opening of the device in the second configuration to thereby inhale an active agent from the membrane of the device through the channel and into the lungs.

16. The method according to claim 15, wherein the user contacts their mouth to the device adjacent to the first opening of the device in the second configuration to thereby form a seal around the first opening before inhaling through the device.

17. The method according to claim 15, wherein the device is locked into the second configuration when the device is moved from the first configuration to the second configuration.

* * * * *